(12) United States Patent
Ducao et al.

(10) Patent No.: US 11,666,217 B2
(45) Date of Patent: Jun. 6, 2023

(54) SYSTEM AND METHOD FOR BIOMETRIC-BASED SPATIAL CATEGORIZATION

(71) Applicant: DuKorp Corp., Brooklyn, NY (US)

(72) Inventors: Arlene Ducao, Brooklyn, NY (US); Ilias Koen, Athens (GR); Christopher Willard, Brooklyn, NY (US); Yapah Berry, Jersey City, NJ (US)

(73) Assignee: DuKorp Corporation, Brooklyn, NY (US)

( * ) Notice: Subject to any disclaimer, the term of this patent is extended or adjusted under 35 U.S.C. 154(b) by 355 days.

(21) Appl. No.: 16/452,823

(22) Filed: Jun. 26, 2019

(65) Prior Publication Data

US 2020/0000337 A1   Jan. 2, 2020

Related U.S. Application Data (60) Provisional application No. 62/692,789, filed on Jul. 1, 2018.

(51) Int. Cl.
| | |
|---|---|
| A61B 5/024 | (2006.01) |
| A61B 5/00 | (2006.01) |
| H04W 4/029 | (2018.01) |
| G06F 16/909 | (2019.01) |
| G06F 16/908 | (2019.01) |
| G06F 16/906 | (2019.01) |
| A61B 5/291 | (2021.01) |

(52) U.S. Cl.
CPC ........ *A61B 5/0022* (2013.01); *A61B 5/02438* (2013.01); *A61B 5/291* (2021.01); *G06F 16/906* (2019.01); *G06F 16/908* (2019.01); *G06F 16/909* (2019.01); *H04W 4/029* (2018.02)

(58) Field of Classification Search
CPC .... G06F 16/909; G06F 16/906; G06F 16/908; A61B 5/00; A61B 5/291; A61B 5/1112; A61B 5/0022; A61B 5/02438; H04W 4/029
USPC ...................................................... 434/236
See application file for complete search history.

(56) References Cited

U.S. PATENT DOCUMENTS

| | | |
|---|---|---|
| 5,842,182 A | 11/1998 | Bonner et al. |
| 7,925,055 B2 | 4/2011 | Kevenaar et al. |

(Continued)

*Primary Examiner* — Allen Porter
*Assistant Examiner* — Skylar Lindsey Christianson
(74) *Attorney, Agent, or Firm* — Blank Rome LLP (57) ABSTRACT

A system includes a biometric device, a biometric data collection device, and a spatial categorization system. The biometric device includes a biometric sensor to measure a biometric trait of a user. The biometric data collection device includes a positioning system and a biometric data storage system, and a third wireless transceiver. The positioning system is configured to provide spatial location values specifying a geographic location of the biometric data collection device. The biometric data storage system is configured to assign time stamp values to each of the spatial location values and biometric trait measurements. The spatial categorization system is configured to identify a biometric trait measurement indicating that a condition of the user has a value that exceeds a threshold, and to assign, based on the identified biometric trait measurement, a category identification value to a spatial region corresponding to the spatial location value.

12 Claims, 8 Drawing Sheets

(56) References Cited

U.S. PATENT DOCUMENTS

| | | |
|---|---|---|
| 8,020,220 B2 | 9/2011 | McElroy et al. |
| 8,121,356 B2 | 2/2012 | Friedman et al. |
| 8,195,203 B1 | 6/2012 | Tseng |
| 8,352,546 B1 | 1/2013 | Dollard |
| 8,396,530 B1 | 3/2013 | Wilder-Smith et al. |
| 8,617,067 B2 | 12/2013 | Jain et al. |
| 8,622,901 B2 | 1/2014 | Jain et al. |
| 8,700,009 B2 | 4/2014 | Quy |
| 8,744,803 B2 | 6/2014 | Park et al. |
| 8,762,101 B2 | 6/2014 | Yuen et al. |
| 8,787,624 B2 | 7/2014 | Hama et al. |
| 8,913,799 B2 | 12/2014 | Hauke et al. |
| 8,971,593 B2 | 3/2015 | Mueller et al. |
| 9,043,345 B2 | 5/2015 | Davis et al. |
| 9,076,125 B2 | 7/2015 | Manolescu et al. |
| 9,135,419 B2 | 9/2015 | Newman et al. |
| 9,171,201 B2 | 10/2015 | Lake, II et al. |
| 9,173,567 B2 | 11/2015 | Jain et al. |
| 9,223,832 B2 | 12/2015 | Hamborg et al. |
| 9,245,229 B2 | 1/2016 | Fadell et al. |
| 9,264,861 B1 | 2/2016 | Arastafar et al. |
| 9,320,449 B2 | 4/2016 | Gu |
| 9,339,188 B2 | 5/2016 | Proud |
| 9,367,628 B2 | 6/2016 | Fechete et al. |
| 9,423,249 B2 | 8/2016 | Deppermann et al. |
| D770,145 S | 11/2016 | Aimone et al. |
| 9,507,974 B1 | 11/2016 | Todeschini |
| D773,154 S | 12/2016 | Aimone et al. |
| 9,563,258 B2 | 2/2017 | Wei |
| 9,579,060 B1 | 2/2017 | Lisy et al. |
| 9,595,016 B1 | 3/2017 | Schwartz et al. |
| 9,629,574 B2 | 4/2017 | Lee |
| 9,642,543 B2 | 5/2017 | Banerjee et al. |
| 9,646,046 B2 | 5/2017 | Sadowsky et al. |
| 9,664,518 B2 | 5/2017 | Mach |
| 9,703,862 B2 | 7/2017 | Burton et al. |
| 9,710,772 B1 | 7/2017 | Kelly et al. |
| D794,282 S | 8/2017 | Aimone et al. |
| 9,730,027 B2 | 8/2017 | Su et al. |
| 9,731,726 B2 | 8/2017 | Gordon et al. |
| 9,740,782 B2 | 8/2017 | Krasnikov |
| 9,788,794 B2 | 10/2017 | LeBoeuf et al. |
| 2014/0206954 A1* | 7/2014 | Yuen .................. A61B 5/0022 600/301 |
| 2015/0262397 A1* | 9/2015 | Eastman ............. G06K 9/6218 345/440 |
| 2017/0124110 A1* | 5/2017 | Hajj ................. H04L 67/2838 |
| 2018/0157980 A1* | 6/2018 | Kochura .............. G06N 5/048 |

\* cited by examiner

SYSTEM AND METHOD FOR BIOMETRIC-BASED SPATIAL CATEGORIZATION

CROSS-REFERENCE TO RELATED APPLICATIONS

The present application claims priority to U.S. Provisional Patent Application No. 62/692,789, filed Jul. 1, 2018, entitled "System and Method for Biometric-Based Spatial Categorization," which is hereby incorporated herein by reference in its entirety.

BACKGROUND

As biosensing technology has become cheaper and easier to use, biosensor use is increasing greatly. For example, biosensors available in wristband form factors are widely used to track electro-dermal activity, measure heart rate or heart rate variability, and other physiological traits. The biometric data produced by such sensors can be used in a wide range of applications including health and fitness tracking, stress monitoring, and entertainment.

SUMMARY

In one example, a system includes a biometric device, a biometric data collection device, and a spatial categorization system. The biometric device includes a biometric sensor, and a first wireless transceiver. The biometric sensor is configured to measure a biometric trait of a user. The first wireless transceiver circuit is configured to transmit biometric trait measurements. The biometric data collection device includes a second wireless transceiver circuit, a positioning system, a biometric data storage system, and a third wireless transceiver circuit. The second wireless transceiver circuit is configured to receive the biometric trait measurements transmitted by the biometric device. The positioning system is configured to provide spatial location values specifying a geographic location of the biometric data collection device. The biometric data storage system is configured to assign time stamp values to each of the biometric trait measurements, and each of the spatial location values. The biometric data storage system is also configured to store the biometric trait measurements, the spatial location values, and the assigned time stamp values. The third wireless transceiver circuit is configured to transmit the biometric trait measurements, the spatial location values, and the assigned time stamp values. The spatial categorization system is configured to receive the biometric trait measurements the spatial location values, and the assigned time stamp values, and to associate each of the biometric trait measurements with one of the spatial location values based on time stamp values. The spatial categorization system is also configured to identify a first of the biometric trait measurements indicating that a first condition of the user has a value that exceeds a first threshold, and to identify a second of the biometric trait measurements indicating that a second condition of the user has a value that exceeds a second threshold. The spatial categorization system is further configured to assign, based on the identified first of the biometric trait measurements, a first category identification value to a first spatial region corresponding to the spatial location value associated with the identified first of the biometric trait measurements, and to assign, based on the identified second of the biometric trait measurement, a second category identification value to a second spatial region corresponding to the spatial location value associated with the identified second of the biometric trait measurements.

In another example, a method includes measuring, by a first biometric sensing device, a first biometric trait of a user. A timestamp is assigned to each measurement of the first biometric trait. Measurements of the first biometric trait are transmitted to a biometric data collection device via a wireless personal area network. Spatial location values defining a spatial location of the biometric data collection device are determined by a positioning system of the biometric data collection device. A timestamp is assigned to each spatial location value. The measurements of the first biometric trait and the spatial location values are transmitted by the biometric data collection device to a spatial categorization system via a wide area network. A first of the measurements of the first biometric trait indicating that a first condition of the user has a value that exceeds a first threshold is identified by the spatial categorization system. A first category identification value is assigned, by the spatial categorization system, based on the first of the measurements of the first biometric trait, to a first spatial region corresponding to a spatial location value associated by the time stamps with the first of the measurements of the first biometric trait.

In a further example, a system includes an electroencephalography (EEG) device, a heart rate measurement device, a biometric data collection device, and a spatial categorization system. The EEG device includes an EEG sensor and first wireless transceiver. The EEG sensor is configured to measure electrical activity in a brain of a user. The first wireless transceiver circuit is configured to transmit EEG measurements. The heart rate measurement device includes a heart rate sensor and a second wireless transceiver circuit. The heart rate sensor is configured to measure heart rate of the user. The second wireless transceiver circuit is configured to transmit heart rate measurements. The biometric data collection device includes a third wireless transceiver circuit, a positioning system, a biometric data storage system, and a fourth wireless transceiver circuit. The third wireless transceiver circuit is configured to receive the EEG measurements and the heart rate measurements. The positioning system is configured to provide spatial location information specifying a geographic location of the biometric data collection device. The biometric data storage system is configured to assign time stamps to the spatial location information, the EEG measurements, and the heart rate measurements, and to store the EEG measurements, the heart rate measurements, and the spatial location information. The fourth wireless transceiver circuit is configured to transmit the EEG measurements, the heart rate measurements, and the spatial location information. The spatial categorization system is configured to receive the EEG measurements, the heart rate measurements, and the assigned spatial location information. The spatial categorization system is also configured to identify a first of the EEG measurements and a first of heart measurements indicating that a first condition of the user has a value that exceeds a first threshold, and identify a second of the EEG measurements and a second of the heart rate measurements indicating that a second condition of the user has a value that exceeds a second threshold. The spatial categorization system is further configured to assign, based on the first of the EEG measurements and the first of heart rate measurements, a first category identification value to a first spatial region corresponding to the spatial location information associated by the time stamps with the first of the EEG measurements and the first of heart rate measurements, and to assign, based on the second of the EEG measurements and the second of ECG measurements, a second category identification value to a second spatial region corresponding to the spatial location information associated by the time stamps with the second of the EEG measurements and the second of heart rate measurements.

BRIEF DESCRIPTION OF THE DRAWINGS

For a detailed description of various examples, reference will now be made to the accompanying drawings in which.

DETAILED DESCRIPTION

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

The systems and methods disclosed herein apply biometric data to categorize the spaces in which human beings operate. The systems of the present disclosure employ biometric sensors, such as electroencephalography (EEG) sensors and/or heart rate sensors (e.g., electrocardiography (ECG) sensors) to measure a user's response to space. The EEG and/or heart rate measurements may indicate how a space affects a user's state of mind. For example, the EEG and/or heart rate measurements may indicate whether a space tends to induce stress or relaxation in a user. Implementations may collect biometric data from any number of users and evaluate the biometric data acquired in a given space to categorize the given space.

Implementations of a biometric-based spatial categorization system include a biometric sensor, such as an EEG sensor or a heart rate sensor coupled to a user, and a biometric data collection device coupled to the biometric sensor. The biometric sensor measures a biometric trait of the user as the user operates in space. For example, an EEG sensor measures electrical brain activity of a user as the user traverses a geographic area. The biometric data collection device is communicatively coupled to the biometric sensor (e.g., by a personal area network, such as BLUETOOTH). The biometric sensor transmits measurements to the biometric data collection device. The biometric data collection device includes a positioning system (e.g., a global positioning system (GPS) receiver, or a local area network (LAN) positioning system) that provides spatial location information to identify the location at which each biometric value is performed. The biometric data collection device stores the biometric values and location information for transmission in bulk to a spatial categorization system.

The spatial categorization system includes a computing system (e.g., a virtual computing system) configured to analyze the biometric values and the spatial location information, and to categorize the spaces defined by the spatial location information based on the biometric values performed in the spatial area and received from one or more biometric data collection devices. For example, the categorization may include determining whether a level of stress induced by a space exceeds a threshold, determining whether a level of relaxation induced by space exceeds a threshold, and assigning a categorization value to the space based on biometric values relative to the thresholds. In some implementations, the categorization values assigned to spaces analyzed may be derived from a vocabulary used to describe a space in a particular context. The spatial categorizations produced by the system may be applied to reconfigure a space to elicit a desired biometric response from users. For example, a space may be configured to produce a higher level of relaxation in users.

Figure 1:
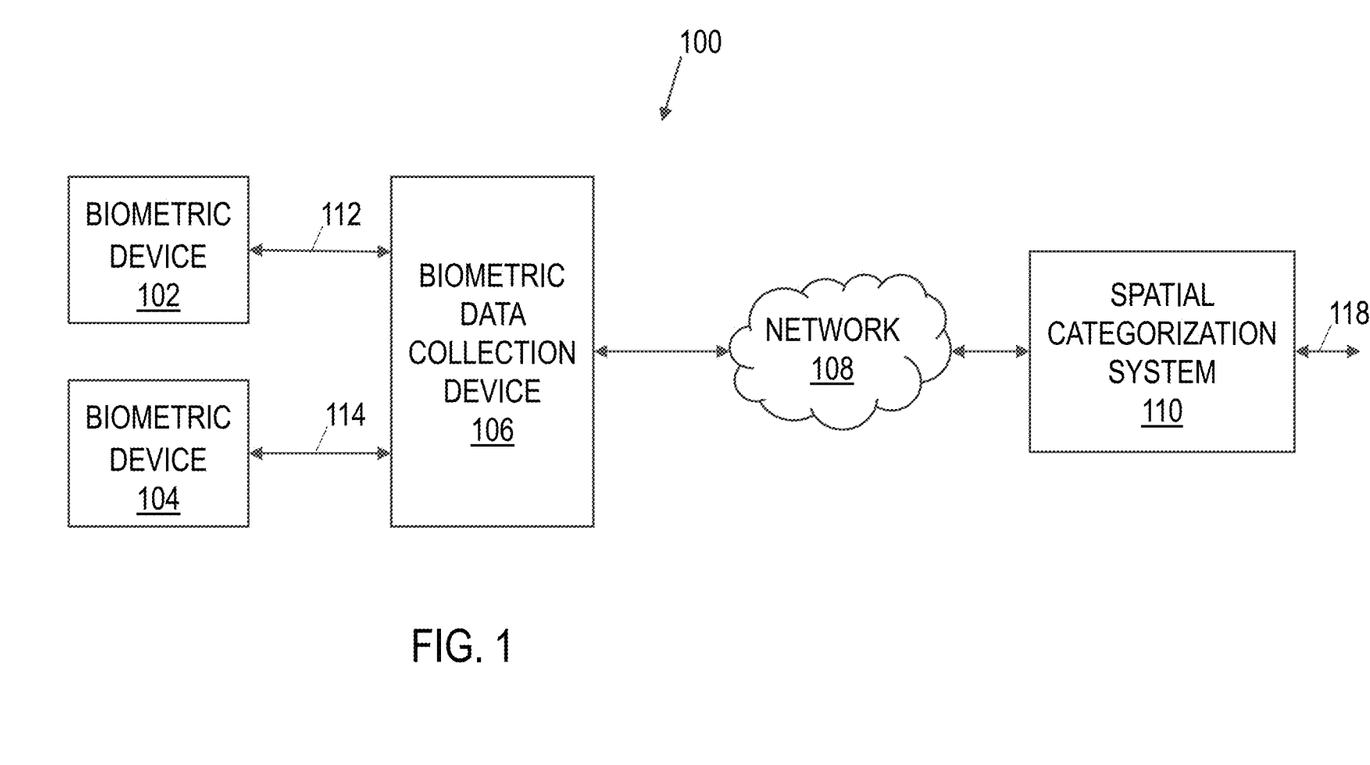
FIG. 1 shows a block diagram for a system that classifies space based on biometric data in accordance with the present disclosure.

FIG. 1 shows a block diagram for a system 100 that classifies space based on biometric data in accordance with the present disclosure. The system 100 includes a biometric device 102, a biometric device 104, a biometric data collection device 106, and a spatial categorization system 110. While the system 100 is illustrated as including two biometric devices (biometric device 102 and biometric device 104), various implementations of the system 100 may include one or more biometric devices. The biometric device 102 and biometric device 104 measure one or more biometric traits of a user to which the biometric device 102 and/or biometric device 104 are attached. For example, the biometric device 102 may be an EEG device that measures electrical activity in a brain of a user, and the biometric device 104 may be a heart rate measurement device that measures heart rate or other cardiac activity of a user by electrical or optical sensing.

The biometric device 102 and the biometric device 104 are communicatively coupled to the biometric data collection device 106. For example, the biometric device 102 and the biometric device 104 may be communicatively coupled to the biometric data collection device 106 via a personal area network, such as a BLUETOOTH wireless network. The biometric device 102 transfers measurements 112 of a biometric trait acquired by the biometric device 102 to the biometric data collection device 106 via the personal area network. Similarly, the biometric device 104 transfers measurements 114 of a biometric trait acquired by the biometric device 104 to the biometric data collection device 106 via the personal area network. The biometric data collection device 106 receives the measurements 112 and measurements 114, and stores the measurements 112 and measurements 114 for transmission to the spatial categorization system 110. The biometric trait measurements 112 and 114 may be stored as received from the biometric devices 102 or 104, or in some implementations of the biometric data collection device 106 the biometric trait measurements 112 and 114 may be stored as values representing a range of values or a category into which each measurement falls. The biometric data collection device 106 includes a positioning system that provides information specifying the location of the biometric data collection device 106. For example, the biometric data collection device 106 may include a global positioning system (GPS) receiver, or other satellite or terrestrial positioning system for determining the location of the biometric data collection device 106. Some implementations of the biometric data collection device 106 may include a positioning system for determining the location of the biometric data collection device 106 within a structure, such as a building. For example, the biometric data collection device 106 may include a positioning system that determines the location of the biometric data collection device 106 based on signal strength of wireless LAN access points or other beacons disposed within a structure. The biometric data collection device 106 stores the location information in association with measurements 112 and biometric device 104 for transmission to the spatial categorization system 110.

Some implementations of the biometric data collection device 106 allow a user to enter comments with regard to a space in which the user is operating to acquire the measurements 112 and measurements 114. For example, the biometric data collection device 106 may allow the user to enter text describing the user's impressions of a space or information regarding conditions in the space that may have affected the measurements 112 and/or the measurements 114. The biometric data collection device 106 stores such comments for transmission to the spatial categorization system 110 with the measurements 112, the measurements 114, and location information provided by the positioning system.

The biometric data collection device 106 transmits the measurements 112, the measurements 114 (i.e., the biometric trait measurements), location information, user comments, etc. to the spatial categorization system 110 via the network 108. The biometric trait measurements may be provided to the spatial categorization system as values received from the biometric devices 102 or 104, or as values representing a range of values or a category into which each measurement falls. The network 108 may be a wide area network, such as a cellular data communication network, the internet, etc.

The spatial categorization system 110 receives the biometric, location, and other information transmitted by the biometric data collection device 106 and analyzes the biometric data to classify or categorize the physical spaces in which the biometric data was acquired. For example, analysis of the measurements 112 and/or the measurements 114 may indicate that the user found a first space to be relaxing and found a second space to be stressful. Thus, the spatial categorization system 110 may categorize a given space as relaxing or stressful based on the measurements 112 and/or the measurements 114 received from the biometric data collection device 106. The spatial categorization system 110 may aggregate the measurements 112 and the measurements 114 with biometric trait measurements received from a plurality of different biometric data collection devices 106 associated with a plurality of different users to classify the various spaces of a geographic area. The spatial categorization system 110 may produce a map 118 that illustrates the classification of spaces shown on the map based on the biometric trait measurements received from one or more instances of the biometric data collection device 106. Such maps may be applied to change or reconfigure a space so as to change the experience of a user operating in the space. For example, if the spatial categorization system 110 classifies a space as stressful based on the measurements 112 and measurements 114, then, responsive to the classification, the space may be reconfigured to reduce the stress associated with the space.

Figure 2:
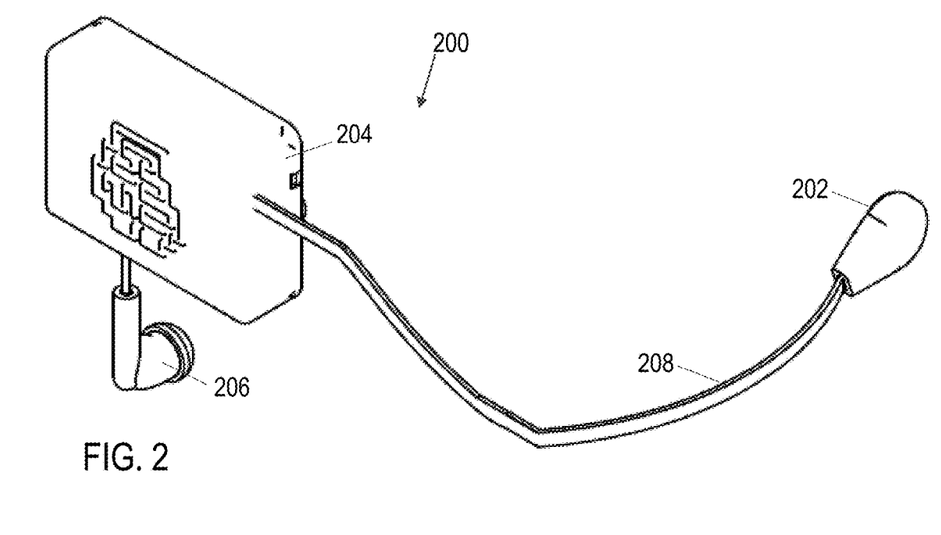
FIG. 2 shows an example of a biometric device for acquiring electroencephalography data in accordance with the present disclosure.

FIG. 2 shows an example of a biometric device 200 for acquiring EEG data in accordance with the present disclosure. The biometric device 200 may be an implementation of the biometric device 102. The biometric device 200 includes an EEG electrode 202, a reference electrode 206, and circuitry 204. The circuitry 204 is coupled to the EEG electrode 202 and the reference electrode 206. The EEG electrode 202 is mounted to an arm 208 that positions the EEG electrode 202 for contact with a user's forehead. The reference electrode 206 captures non-brain electrical signals that provide a reference for the signals captured by the EEG electrode 202. The reference electrode 206 may also provide a ground reference for the EEG electrode 202. In some implementations, the reference electrode 206 may be configured for attachment to an ear or the user. The circuitry 204 includes circuitry to digitize signals detected by the EEG electrode 202, and a transceiver to communicate with the biometric data collection device 106 via a personal area network. For example, the circuitry 204 may include an analog-to-digital converter and signal conditioning circuitry to process EEG signals, and a BLUETOOTH transceiver to communicate EEG signals detected by the EEG electrode 202 to the biometric data collection device 106. The biometric device 200 also includes additional circuits and components, such as batteries and power supplies.

Figure 3:
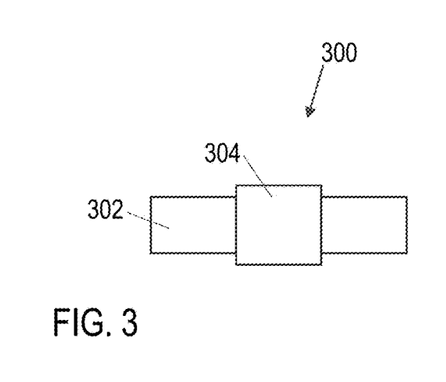
FIG. 3 shows an example of a biometric device for acquiring electrocardiography data in accordance with the present disclosure.

FIG. 3 shows an example of a biometric device 300 for acquiring cardiac data in accordance with the present disclosure. The biometric device 300 may be an implementation of the biometric device 104. The biometric device 300 includes a band 302 and a cardiac sensor 304. The band 302 may be, for example, a chest band or a wrist band. The cardiac sensor 304 may include an ECG electrode to measure cardiac electrical signals, or an optical electrode to measure blood flow, from which heart rate and/or changes in heart rate can be determined. The cardiac sensor 304 also includes a transceiver to communicate with the biometric data collection device 106 via a personal area network. For example, the cardiac sensor 304 may include a BLUETOOTH transceiver to communicate cardiac signals to the biometric data collection device 106. The biometric device 300 also includes additional circuits and components, such as batteries and power supplies.

Figure 4:
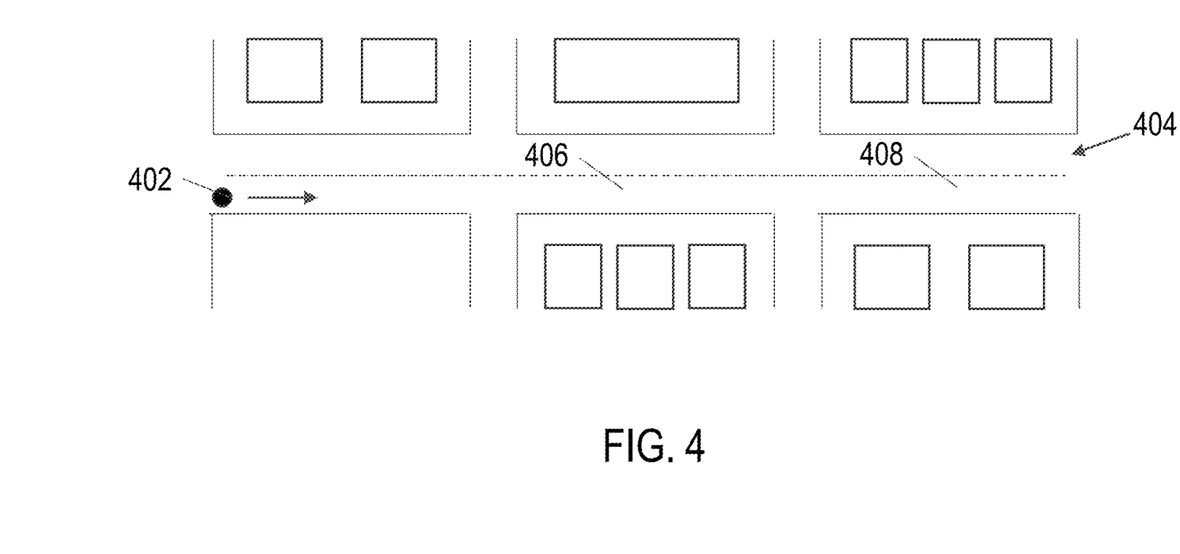
FIG. 4 shows an example of acquisition of biometric data in a spatial environment in accordance with the present disclosure.

FIG. 4 shows an example of acquisition of biometric data in a spatial environment in accordance with the present disclosure. In FIG. 4, a user 402 is outfitted with a biometric device 200 and/or a biometric device 300, and a biometric data collection device 106 that collects biometric data from the biometric device 200 and/or biometric device 300, acquires location information, and generates time of acquisition information (i.e., timestamps). As the user 402 moves along the street 404, on foot, on a bicycle, or in/on a motor vehicle, the biometric device 200 and/or the biometric device 300 measure a biometric trait (e.g., electrical brain activity, heart rate, etc.) of the user 402. For example, the biometric device 200 and the biometric device 300 may measure the electrical brain signals and heart rate of the user 402 one or more times per second (e.g., measure EEG activity 512 times per second). As the user 402 moves along the street 404, the environment around the user 402 produces changes in the user 402 that are reflected in the biometric data. For example, heavy traffic or other conditions in space 406 may result in increased stress in the user 402 that is reflected in the biometric data, while conditions in space 408 may produce increased relaxation in the user 402. The biometric data transferred from the biometric device 200 and the biometric device 300 to the biometric data collection device 106 as the user 402 moves along the street 404 is transmitted to the spatial categorization system 110 for aggregation and analysis either automatically or at a time selected by the user 402.

Figure 5:
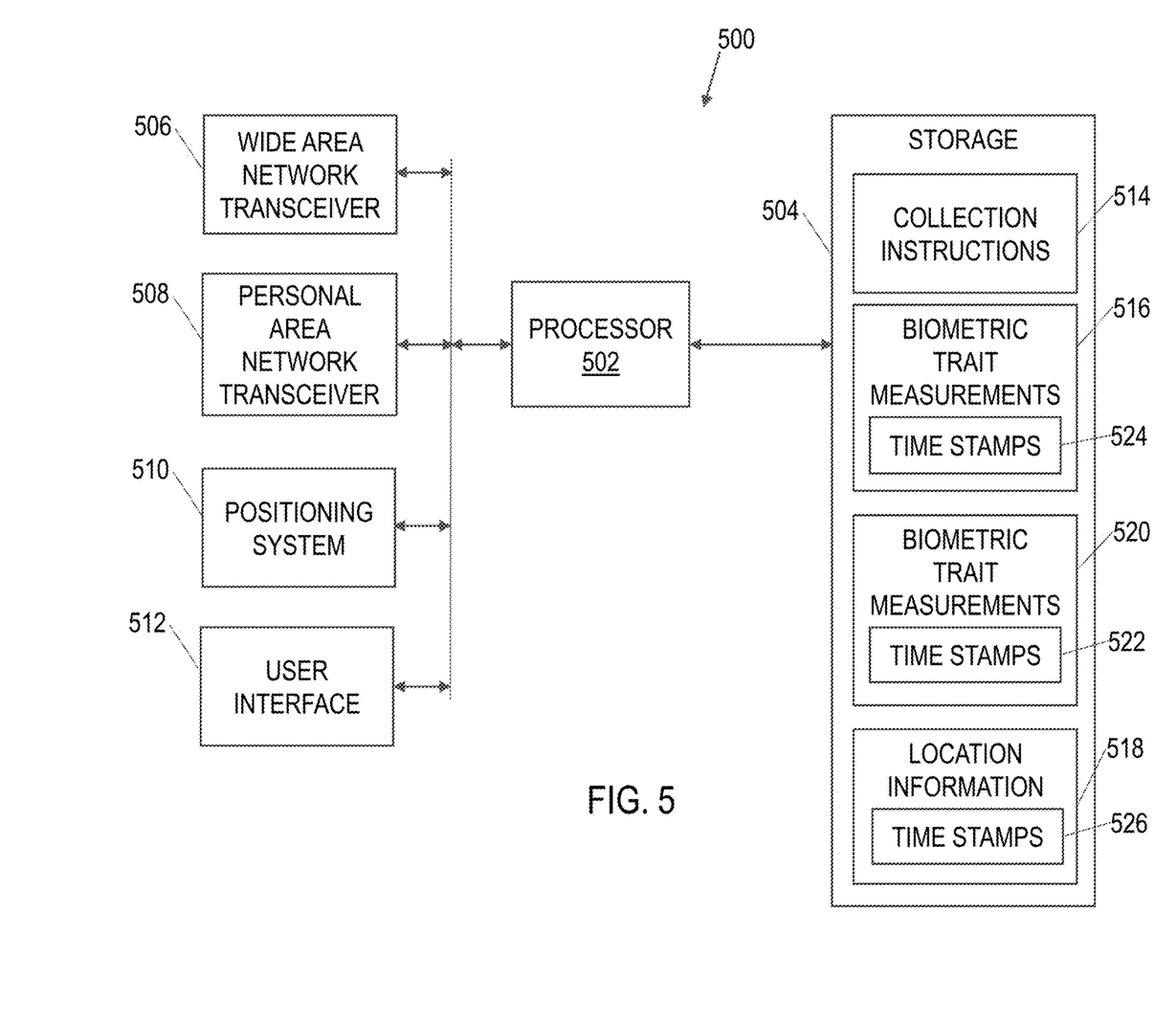
FIG. 5 shows a block diagram for an example of a biometric data collection device in accordance with the present disclosure.

FIG. 5 shows a block diagram for an example of a biometric data collection device 500 in accordance with the present disclosure. The biometric data collection device 500 is an implementation of the biometric data collection device 106. The biometric data collection device 500 includes a processor 502, storage 504, a wide area network transceiver 506, a personal area network transceiver 508, a positioning system 510, and user interface circuitry 512. The processor 502 may be a general-purpose microprocessor or a microcontroller that executes instructions retrieved from the storage 504 to perform the functions disclosed herein.

The wide area network transceiver 506 includes circuitry that allows the biometric data collection device 500 to access a wide area network and communicate with other devices and systems via the wide area network. For example, the wide area network transceiver 506 may include receiver circuitry and transmitter circuitry that enable communication via a cellular data network (e.g., an LTE network). The biometric data collection device 500 applies the wide area network transceiver 506 to communicate with the spatial categorization system 110.

The personal area network transceiver 508 includes circuitry that allows the biometric data collection device 500 to access a personal area network and communicate with other devices and systems via the personal area network. For example, the personal area network transceiver 508 may include receiver circuitry and transmitter circuitry that enable communication via a BLUETOOTH network. The biometric data collection device 500 applies the personal area network transceiver 508 to communicate with the biometric device 102 and/or the biometric device 104.

The positioning system 510 includes circuitry that determines the spatial location of the biometric data collection device 500. For example, the positioning system 510 may include a GPS receiver, a GLONASS receiver, or other receiver for receiving signals from a satellite or terrestrial positioning system transmitter. In implementations of the biometric data collection device 500 that support positioning within a structure, such as a building, the positioning system 510 may include circuitry to determine the location of the biometric data collection device 500 based on LAN access point signal, beacon signal, dead reckoning, or other suitable interior positioning technology. For example, an implementation of the positioning system 510 may include a GPS receiver and LAN based positioning.

The user interface circuitry 512 includes circuitry that allows a user to interact with the biometric data collection device 500. For example, the user interface circuitry 512 may include display circuitry, such liquid crystal display (LCD) circuitry, organic light emitting diode (OLED) display circuitry, etc. for presenting information to the user. The user interface circuitry 512 may include input circuitry, such as capacitive touch screen circuitry to allow the user to enter data into and control the biometric data collection device 500.

The storage 504 is a non-transitory computer-readable medium that stores instructions executed by the processor 502 and data processed by the processor 502. The storage 504 may include non-volatile storage, such as read-only memory, FLASH memory, etc., and volatile memory, such as dynamic random-access memory (DRAM), static random-access memory (SRAM), etc. The storage 504 includes collection instructions 514 that are executed by the processor 502 to process biometric trait measurements 516 and biometric trait measurements 520 received from the biometric device 200 and/or biometric device 300. Such processing may include assigning time stamps 524 to the biometric trait measurements 516, and assigning time stamps 522 to the biometric trait measurements 520. The biometric trait measurements 516 and 520 with associated time stamps 524 and 522 are stored in the storage 504, and transmitted to the spatial categorization system 110 via the wide area network transceiver 506.

The storage 504 also stores the location information 518. The location information 518 is provided by the positioning system 510, and specifies the location of the biometric data collection device 500 when the biometric trait measurements 516 and/or the biometric trait measurements 520 were acquired. The processor 502 retrieves the location information 518 from the storage 504 for transmission to the spatial categorization system 110 via the wide area network transceiver 506.

Other information, such as comments entered by the user, may also be stored in the storage 504, and retrieved therefrom for transmission to the spatial categorization system 110 via the wide area network transceiver 506.

Figure 6:
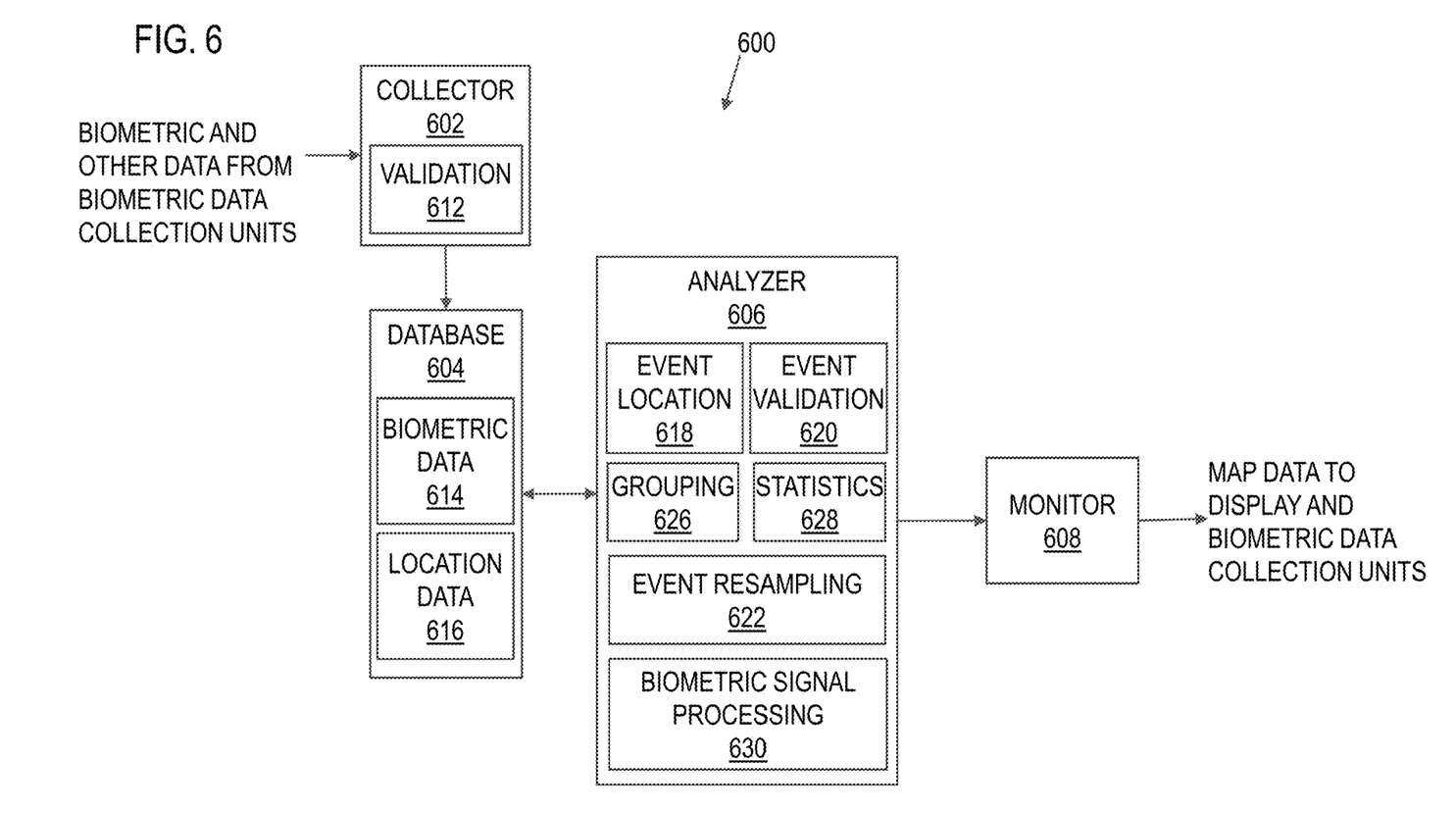
FIG. 6 shows a block diagram for an example of a spatial categorization system in accordance with the present disclosure.

FIG. 6 shows a block diagram for an example of a spatial categorization system 600 in accordance with the present disclosure. The spatial categorization system 600 is an implementation of the spatial categorization system 110. The spatial categorization system 600 includes a collector 602, a database 604, an analyzer 606, and a monitor 608. The collector 602 receives packets of biometric and other data from one or more biometric data collection device devices 500. The packets may include the biometric trait measurements 516, the biometric trait measurements 520, and the location information 518. The packets received from the biometric data collection device 500 may be compressed by the biometric data collection device 500 to reduce the amount of data transmitted. The collector 602 decompresses the received packets, and a validation unit 612 validates the packet data. Validation provided by the validation unit 612 may include checking the data received in each packet to ensure that each field corresponds to an expected data or event type. For example, a field identified as EEG data may include a predetermined number of EEG values, a timestamp field identifier, a timestamp value, an activity type identifier and activity type value. A field identified as location data may include a timestamp field identifier, a timestamp value, latitude, longitude, and altitude identifiers, and latitude, longitude, and altitude values.

After the collector 602 has validated the fields of a packet received from a biometric data collection device 500, the collector 602 transmits a handshake signal to the biometric data collection device 500 that provided the packet, and transfers the contents of the packet to the database 604. The database 604 may include a relational database, an object-oriented database, a NoSQL database, or any other type of database suitable for providing storage and retrieval of the biometric data 614 and the location data 616 received from any number of the biometric data collection device devices 500.

The analyzer 606 processes the biometric data 614 and location data 616 stored in the database 604 to categorize the spaces specified by the location information in accordance with the user condition(s) derived from the biometric data 614. The analyzer 606 determines the spatial location at which each biometric trait measurement of the biometric data 614 was acquired by correlating the time stamps of the biometric trait measurements to the time stamps of the location information of the location data 616. The analyzer 606 includes event location 618, event validation 620, grouping 626, event resampling 622, and biometric signal processing 630.

The event location 618 applies the time stamps 524 and 526 provided with the biometric trait measurements 516 and the location information 518 to determine the spatial location at which each biometric trait measurement was acquired. For example, a location having a time stamp nearest to the time stamp of a biometric trait measurement may be deemed to be the location at which the biometric trait measurement was acquired.

The event validation 620 identifies biometric trait measurements provided by the event location 618 that conform to various acquisition rules. For example, rules for acquisition of biometric trait measurements may require that measurements be made within a predetermined geographic area, that the speed of the user while operating in the predetermined geographic area be within a specified range, and/or that the amplitude of the biometric signals acquired be above a specified threshold. Biometric trait measurements not conforming to the rules of acquisition may be discarded or excluded from use in further processing.

In some implementations of the analyzer 606, the event validation 620 provides signal validation and spatial validation. In the signal validation process, the validation unit applies signal processing and analysis tools to compare a continuous, periodic biosensor signal (dependent variable) to other relevant (explanatory) variables, including biosensor signals, post-processed signals (e.g. attention, meditation, and heart rate based on the manufacturer's algorithm), and sentiment indicators (e.g. in-app survey responses). Examining if the biosensor signal demonstrates significant patterns when compared to other variables helps to determine whether the signal is too noisy to use in further analysis. For example, raw EEG signals may be used to validate other biometric data. Operations of the signal validation process may include:

Preparing and cleaning the EEG raw (dependent) and Heart rate, GPS, and data (independent) for analysis. Implementations of the event validation 620 may use Python for analysis, including a variety of analysis libraries.

Determining thresholds of interest in the independent variable (e.g. heart rate>80 bpm, speed>25 kph).

Epoching the EEG data (dependent variable) based on those threshold events. This includes bandpass filtering and signal transformations (e.g. Hilbert, Fourier). The band power frequencies listed in Table 1 may be used in some implementations.

Running temporal regressions and/or outputting histograms to look for significant relationships.

TABLE 1

EEG Band Power Associations

| Band Power | Frequencies | Association |
| --- | --- | --- |
| Delta | 0.1-3 Hertz | Sleep |
| Theta | 4-7 Hertz | Drowsiness and Idling |
| Alpha (low/high) | 8-12 Hertz | Daydreaming, mindfulness |
| Beta (low/high) | 12-30 Hertz | Active thinking, motor behavior, focus, alertness |
| Gamma (low/high) | 30-100 Hertz | Short-term memory, recognition of objects |

In spatial validation, local and global spatial autocorrelation and other spatial techniques are used to test the spatial distribution of the collected data, including biosensor signals and sentiment indicators to evaluate the likelihood that the spatial distribution of a given dataset is random or not random. The greater the likelihood that the dataset is not distributed randomly, the better the dataset is for use in spatial regression and modeling with explanatory variables. For the spatial validation process, the event validation 620 may use the Python Spatial Analysis Library (PySAL), Pandas, GeoPandas, and Shapely. Spatial analysis operations include:

Subdividing the study area into manageable partitions. Some implementations overlay a grid (e.g., a grid with 150 square foot grid cell size) on the study area. This allows for spatial results that showed high enough resolution to differentiate between street-sized areas, but low enough resolution to be able to process all the biometric datasets. Some implementations divide the study area by actual streets, which may best reflect the reality of the data collection methodology and yield high-resolution spatial results.

Processing spatial weights matrices for each data type. A spatial weights matrix quantifies the spatial relationships that exist among the features in a dataset. Some implementations apply a grid-based contiguity approach, using the "Queen" methodology, in which features only need to share one point to be considered adjacent.

Using the spatial weights calculation to process spatial autocorrelation and spatial lag for each data type in order to understand the data's spatial relationship to the study area; specifically, whether similar and dissimilar features tend to cluster or disperse, and the probability that the clustering or dispersion is the result of random chance.

Processing local indicators of spatial association (LISA) to show statistically significant areas of clustering and dispersion for dissimilar and similar features.

The results of the spatial autocorrelation and the LISA process show whether a spatial regression model is an appropriate next step.

The biometric signal processing 630 processes the biometric trait measurements output by the event validation 620 to prepare for spatial categorization. Signal and spatial validation help to clarify a biosensor dataset's relevance and utility to be included as part of a larger spatial model, in which spatial statistics are employed on all collected data to model how the collected data, namely the biosensor and sentiment indicators from the data collection devices 106, relate to exogenous data. Exogenous data may include information related to motor vehicle collisions, citizen service requests, bike routes, street types, speed limit, street density, subway entrances, tree counts, and other data acquired from sources other than the data collection devices 106. Some implementations of the biometric signal processing 630 apply linear regression to examine the relationship of endogenous and exogenous data.

The operations of spatial modeling include:
- Fetching endogenous data (collected by the data collection device 106) from the database 604.
- Fetching exogenous data, for the same date range as the endogenous data from appropriate sources external to the spatial categorization system 600.
- Applying grid (e.g., a 150-meter grid) that bounds the geographic area in which the endogenous data was acquired.
- Using the grid to subdivide both exogenous and endogenous data sets.
- Serializing and caching all "gridified" data sets to facilitate their use during and between interactive analysis sessions. This is especially beneficial for endogenous biometric datasets, which may be tens of gigabytes in size. Exogenous data, collected at much lower frequencies than the endogenous biometric and sentiment data, are generally much more manageable in size than the endogenous data, but serializing and caching all fetched data helps to speed the runtime of the exploratory regression.
- Loading all cached data.
- Spatially joining exogenous data, endogenous data, and the grid.
- Cleaning up artifacts (non-data columns) derived from the spatial join.
- Trimming the joined data to the study area.
- Running a regression (e.g., an OLS (ordinary least squares) regression) on the joined data. For each regression, one endogenous data type (e.g. EEG low beta) is chosen as the dependent variable, and a short list of around 10 exogenous data types are chosen as independent variables.
- Evaluating the results and removing independent variables from the model.

In some implementations of the biometric signal processing 630, the EEG measurements are pre-processed and filtered into bands (e.g., gamma, beta, alpha, theta, and/or delta). The pre-processing may include electro-oculogram (EOG) processing to remove eye blinks artifacts from the EEG data, and/or applying interpolation to fill gaps in the EEG data. The condition (a level of stress, relaxation, etc.) of the user is derived from the amplitude of the EEG signal in one or more bands. For example, the amplitude (or power) of the EEG signal in the various bands may be compared to thresholds, where the thresholds applied to each band are indicative of various conditions of the user. Similarly, heart rate, or changes in heart rate, may be compared to thresholds that are indicative of various conditions of the user. Thus, the biometric signal processing 630 may determine a condition of each user in a space based on the biometric trait measurements acquired for the user while in the space.

The biometric signal processing 630 categorizes space based on the conditions assigned to users operating in the space. For example, given data from multiple users operating in a space, the biometric signal processing 630 may average condition values, apply a majority condition value, or most frequent condition value to assign a category identification value to a space. Category identification values assigned to spaces may correspond to the user condition values from which the category identification values are derived. For example, a category identification value of "stressful" may result from a user condition indicating stress. Similarly, a category identification value of "relaxed" may result from the user condition indicating relaxation. In some implementations, a value of condition is compared to one or more threshold values to select a category identification value. For example, a user condition value may indicate a variable degree of relaxation. If the condition value exceeds a threshold, then a category identification value for a corresponding space may be set to indicate that the space induces relaxation. Similarly, a user condition value may indicate a variable degree of stress. If the condition value exceeds a threshold, then a category identification value for a corresponding space may be set to indicate that the space induces stress. Implementations of the biometric signal processing 630 may assign a variety of condition values and category identification values to represent user conditions and an attribute of a physical space, stress and relaxation are only two examples of condition values and category identification values that may be applied in implementations of the system 100.

The grouping 626 identifies (or groups) the biometric trait measurements and associated location information selected by the event validation 620 as conforming to the rules of acquisition that were acquired from a given user. That is, the grouping 626 groups by user the biometric trait measurements and associated location information validated by the event validation 620.

The event resampling 622 resamples (e.g., decimates) the biometric trait measurements and associated location information selected by the event validation 620 to reduce the number of measurements used to generate a map displaying the geographic area over which biometric trait measurements are to be acquired and the specific locations within the geographic area at which biometric trait measurements have been acquired.

The statistics 628 generate, from the output of the grouping 626, ranking for each user (e.g., each user in relation to other users) based on the received biometric trait measurements (e.g., the quantity of measurements and/or size of space traversed). The 628 statistics may also generate for each user a summary of activity detailing the user's notes and comments, validated biometric trait measurements, usage of the biometric data collection device 106, etc.

Figure 9:
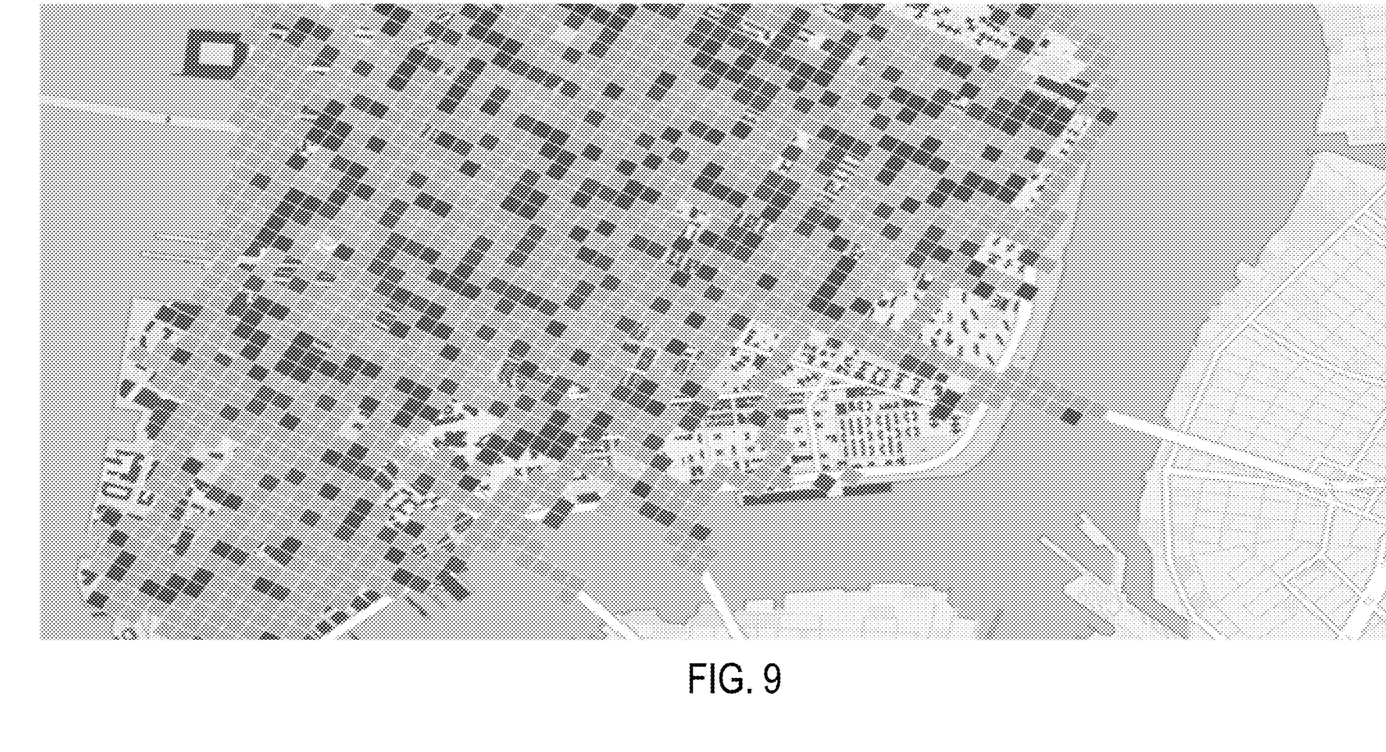
FIG. 9 shows an example of a map of a geographic area that includes spatial categorization based on biometric trait measurements in accordance with the present disclosure.

The monitor 608 applies the output of the analyzer 606 to generate a map of a geographic area. The map includes a representation of a spatial area (e.g., streets, blocks, building interior, or other area) to be categorized based on the biometric trait measurements acquired by the system 100. The monitor 608 overlays on the representation of the spatial area identification values the category identification values generated by the biometric signal processing 630 based on the condition of one or more users derived from biometric trait measurements collected in the geographic area. For example, in a first space in which the biometric trait measurements indicate a user exhibits a first condition (e.g., relaxation), the monitor 608 may add a first color to the map as representative of a first category identification value, while in a second space in which the biometric trait measurements indicate a user exhibits a second condition (e.g., stress), the monitor 608 may add a second color to the map as representative of a second category identification value. FIG. 9 shows an example of a map of a geographic area divided in a number of subareas (e.g., blocks), and each block assigned a category identification value (e.g., a color value) that indicates a condition of one or more users of the system 100 operating in the subarea.

Some implementations of the monitor 608 may also generate a list of all users of the system 100 present in a geographic area on any given day. The list may include a variety of data provided by each user. Such data may include: number of EEG samples provided, number of heart rate samples provided, number of minutes operating in the area, etc.

The monitor 608 may also provide an individualized display for each user that is viewable via the biometric data collection device 106 or a web page. The individualized display may show spaces in which the user has acquired biometric trait measurements, and/or a summary of the data provided by the user as generated by the statistics 628.

Figure 7:
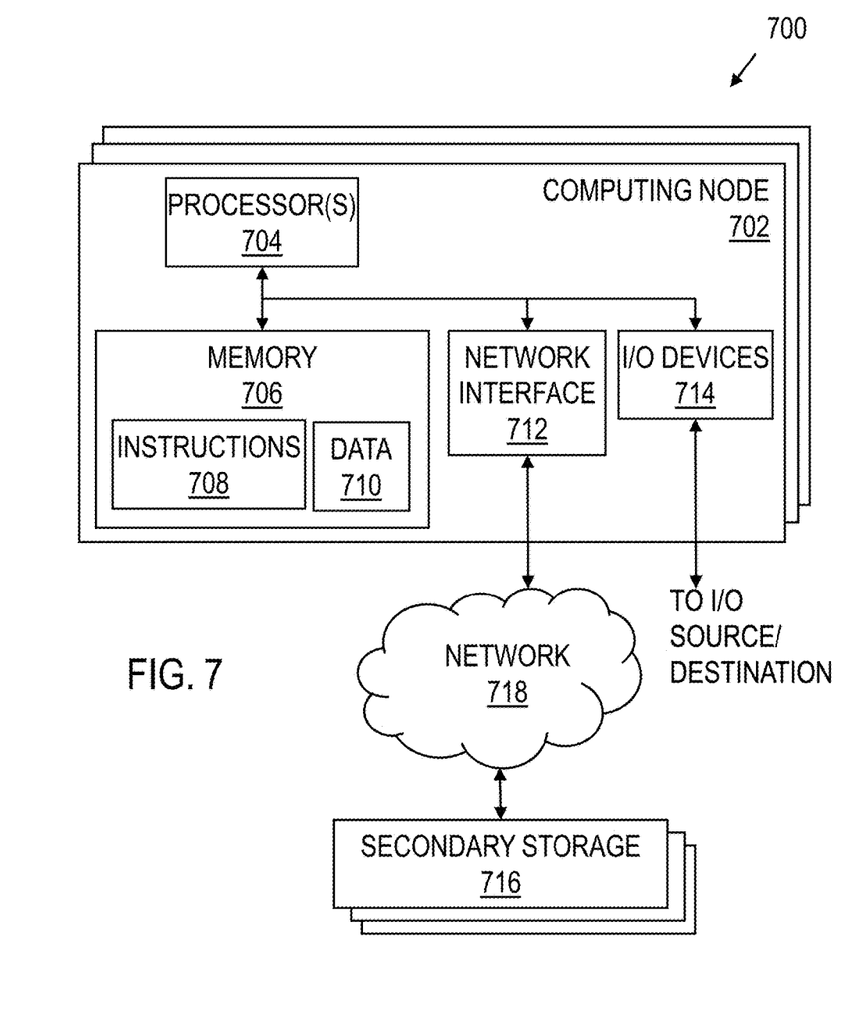
FIG. 7 shows a schematic diagram for a computing system suitable for implementation of a spatial categorization system in accordance with the present disclosure.

FIG. 7 shows a schematic diagram for a computing system 700 suitable for implementation of the spatial categorization system 600. The computing system 700 includes one or more computing nodes 702 and secondary storage 716 that are communicatively coupled via a network 718. One or more of the computing nodes 702 and associated secondary storage 716 may be applied to provide the functionality of the spatial categorization system 600, including the collector 602, the database 604, the analyzer 606, the monitor 608, etc.

Each computing node 702 includes one or more processors 704 coupled to memory 706, network interface 712, and I/O devices 714. In some embodiments of the spatial categorization system 600, a computing node 702 may implement the functionality of more than one component of the spatial categorization system 600. In various embodiments, a computing node 702 may be a uniprocessor system including one processor 704, or a multiprocessor system including several processors 704 (e.g., two, four, eight, or another suitable number). Processors 704 may be any suitable processor capable of executing instructions. For example, in various embodiments, processors 704 may be general-purpose or embedded microprocessors implementing any of a variety of instruction set architectures (ISAs), such as the x86, PowerPC, SPARC, or MIPS ISAs, or any other suitable ISA. In multiprocessor systems, each of processors 704 may commonly, but not necessarily, implement the same ISA. Similarly, in a distributed computing system such as one that collectively implements the spatial categorization system 600, each of the computing nodes 702 may implement the same ISA, or individual computing nodes and/or replica groups of nodes may implement different ISAs.

The memory 706 may include a non-transitory computer-readable storage medium configured to store program instructions 708 and/or data 710 accessible by processor(s) 704. The memory 706 may be implemented using any suitable memory technology, such as static random-access memory (SRAM), synchronous dynamic RAM (SDRAM), nonvolatile/Flash-type memory, or any other type of memory. Program instructions 708 and data 710 implementing the functionality disclosed herein are stored within system memory 706. For example, instructions 708 may include instructions that when executed by processor(s) 704 implement the collector 602, the database 604, the analyzer 606, the monitor 608, and/or other components of the spatial categorization system 600 disclosed herein.

Secondary storage 716 may include volatile or non-volatile storage and storage devices for storing information such as program instructions and/or data as described herein for implementing the spatial categorization system 600. The secondary storage 716 may include various types of computer-readable media accessible by the computing nodes 702 via the network 718. A computer-readable medium may include storage media or memory media such as semiconductor storage, magnetic or optical media, e.g., disk or CD/DVD-ROM, or other storage technologies. Program instructions and data stored on the secondary storage 716 may be transmitted to a computing node 702 for execution by a processor 704 by transmission media or signals via the network 718, which may be a wired or wireless network or a combination thereof.

The network interface 712 may be configured to allow data to be exchanged between computing nodes 702 and/or other devices coupled to the network 718 (such as other computer systems, communication devices, input/output devices, or external storage devices). The network interface 712 may support communication via wired or wireless data networks, such as any suitable type of Ethernet network, for example; via telecommunications/telephony networks such as analog voice networks or digital fiber communications networks; via storage area networks such as Fibre Channel SANS, or via any other suitable type of network and/or protocol.

Input/output devices 714 may include one or more display terminals, keyboards, keypads, touchpads, scanning devices, voice or optical recognition devices, or any other devices suitable for entering or retrieving data by one or more computing nodes 702. Multiple input/output devices 714 may be present in a computing node 702 or may be distributed on various computing nodes 702 of the system 700. In some embodiments, similar input/output devices may be separate from computing node 702 and may interact with one or more computing nodes 702 of the system 100 through a wired or wireless connection, such as over network interface 712.

Those skilled in the art will appreciate that computing system 700 is merely illustrative and is not intended to limit the scope of embodiments. In particular, the computing system 700 may include any combination of hardware or software that can perform the functions disclosed herein, including computers, network devices, Internet appliances, PDAs, wireless phones, pagers, etc. Computing node 702 may also be connected to other devices that are not illustrated, in some embodiments. In addition, the functionality provided by the illustrated components may in some embodiments be combined in fewer components or distributed in additional components. Similarly, in some embodiments the functionality of some of the illustrated components may not be provided and/or other additional functionality may be available.

Figure 8:
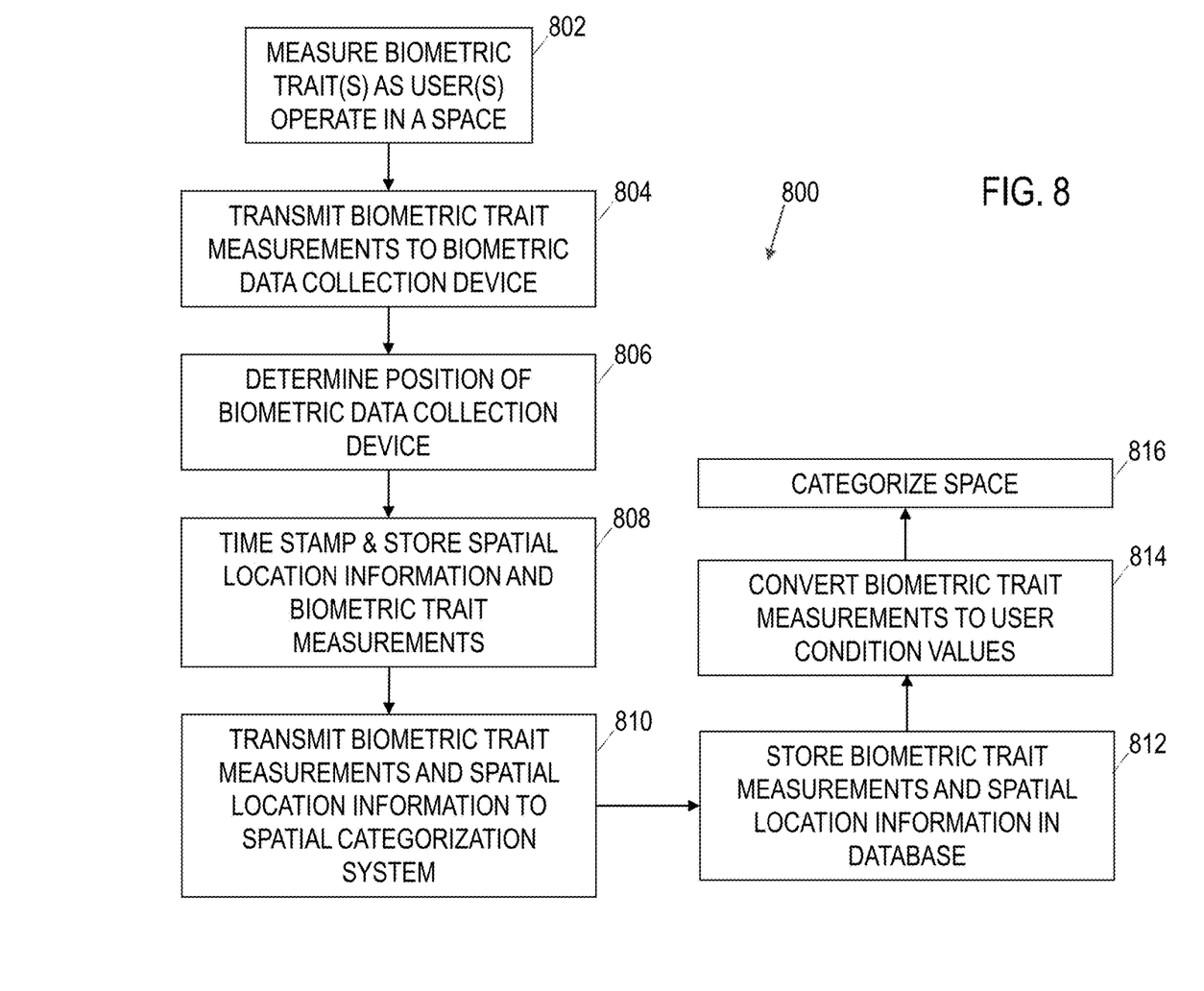
FIG. 8 show a flow diagram for a method for spatial categorization based on biometric trait measurements in accordance with the present disclosure.

FIG. 8 shows a flow diagram for a method 800 for spatial categorization in accordance with the present disclosure. Though depicted sequentially as a matter of convenience, at least some of the actions shown can be performed in a different order and/or performed in parallel. Additionally, some implementations may perform only some of the actions shown. Operations of the method 800 may be performed by implementations of the system 100.

In block 802, one or more users are operating in a space, and the biometric device 102 and/or the biometric device 104 attached to the users are measuring biometric traits, such as brain electrical activity or heart rate each user.

In block 804, the biometric device 102 and/or the biometric device 104 transmit the acquired biometric trait measurements to a biometric data collection device 106. The biometric data collection device 106 may be carried by or otherwise located proximate the user.

In block 806, the biometric data collection device 106 determines the geographic location of the biometric data collection device 106 while the biometric device 102 and/or the biometric device 104 are acquiring biometric trait measurements.

In block 808, the biometric data collection device 106 time stamps the location information generated in block 806 and the biometric trait measurements received from the biometric device 102 and/or the biometric device 104. The time stamped location information and biometric trait measurements are stored in internal memory of the biometric data collection device 106.

In block 810, the biometric data collection device 106 transmits the time stamped location information and biometric trait information to the spatial categorization system 110.

In block 812, the spatial categorization system 110 stores the stamped location information and biometric trait information in a database 604 of the spatial categorization system 110.

In block 814, the spatial categorization system 110 retrieves the stamped location information and biometric trait information from the database 604 and associates the biometric trait measurements with a physical space by correlation of the time stamps assigned to the location information and the biometric trait information. The spatial categorization system 110 processes the biometric trait measurements to produce values that assign a condition to the user.

In block 816, the spatial categorization system 110 categorizes one or more spaces based on the conditions assigned to users in the spaces based on the biometric trait measurements acquired in the spaces.

Those skilled in the art will also appreciate that in some embodiments the functionality disclosed herein may be provided in alternative ways, such as being split among more software modules or routines or consolidated into fewer modules or routines. Similarly, in some embodiments illustrated methods may provide more or less functionality than is described, such as when other illustrated methods instead lack or include such functionality respectively, or when the amount of functionality that is provided is altered. In addition, while various operations may be illustrated as being performed in a particular manner (e.g., in serial or in parallel) and/or in a particular order, those skilled in the art will appreciate that in other embodiments the operations may be performed in other orders and in other manners. The various methods as depicted in the figures and described herein represent illustrative embodiments of methods. The methods may be implemented in software, in hardware, or in a combination thereof in various embodiments. Similarly, the order of any method may be changed, and various elements may be added, reordered, combined, omitted, modified, etc., in various embodiments.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system, comprising:
 a biometric device, comprising:
  a biometric sensor configured to measure a biometric trait of a user at least 512 times per second; and
  a first wireless transceiver circuit configured to transmit biometric trait measurements;
  wherein the biometric device is an electroencephalography (EEG) device, the biometric sensor is an EEG sensor, and the biometric trait is electrical activity in a brain of the user;
 a biometric data collection device comprising:
  a second wireless transceiver circuit configured to receive the biometric trait measurements transmitted by the biometric device;
  a positioning system configured to provide spatial location values specifying a geographic location of the biometric data collection device;
  a biometric data storage system configured to:
   assign time stamp values to:
    each of the biometric trait measurements; and
    each of the spatial location values;
   store the biometric trait measurements, the spatial location values, and the assigned time stamp values; and
  a third wireless transceiver circuit configured to transmit the biometric trait measurements, the spatial location values, and the assigned time stamp values;
 a spatial categorization system comprising:
  a database configured to store the biometric trait measurements and the spatial location information;
  a collection unit configured to:
   receive information from the biometric data collection device, the information comprising the biometric trait measurements, the spatial location values, and the assigned time stamp values;
   decompress the information;
   validate the information;
   store the information in the database; and
   notify the biometric data collection device of receipt of the information;
  an analysis unit configured to:
   retrieve from the database, information comprising:
    a biometric dataset including at least 10 gigabytes of the biometric trait measurements;
    the spatial location values;
    the assigned time stamp values;
    attribute data corresponding to the spatial locations defined by the spatial location information; and
    user comments directed to the spatial locations at which the biometric trait measurements are acquired;
   process each of the biometric trait measurements of the biometric dataset to:
    associate each of the biometric trait measurements with one of the spatial location values based on the assigned time stamp values;
    identify each first of the biometric trait measurements, wherein each first of the biometric trait measurements indicates that a first condition of the user has a value that exceeds a first threshold;
    identify each second of the biometric trait measurements, wherein each second of the biometric trait measurements indicates that a second condition of the user has a value that exceeds a second threshold;
    assign, based on the identified first of the biometric trait measurements, a first category identification value to a first spatial region corresponding to the spatial location value associated with the identified first of the biometric trait measurements; and assign, based on the identified second of the biometric trait measurement, a second category identification value to a second spatial region corresponding to the spatial location value associated with the identified second of the biometric trait measurements; and a monitor configured to generate a map of a geographic area including:

an indicator of the first category identification value in the first spatial region; and an indicator of the second category identification value in the second spatial region.

2. The system of claim 1, wherein the first wireless transceiver circuit and the second wireless transceiver circuit are configured to communicate via personal area network.

3. The system of claim 1, wherein the third wireless transceiver circuit is configured to communicate via a wide area network.

4. The system of claim 1, wherein the biometric data collection device is a cellular handset.

5. The system of claim 1, wherein the biometric device is a first biometric device and the biometric trait is a first biometric trait, and biometric trait measurements are first biometric trait measurements, and the system further comprises:

a second biometric device, comprising:

a second biometric sensor configured to measure a second biometric trait of the user; and a fourth wireless transceiver circuit configured to transmit second biometric trait measurements corresponding to the second biometric trait to the biometric data collection device.

6. The system of claim 5, wherein the second biometric sensor is a heart rate sensor.

7. The system of claim 5, wherein the spatial categorization system is configured to:

receive the second biometric trait measurements and time stamp values assigned to the second biometric trait measurements;

associate each of the second biometric trait measurements with one of the spatial location values based on time stamp values;

identify a first of the second biometric trait measurement indicating that the first condition of the user has a value that exceeds the first threshold;

identify a second of the second biometric trait measurements indicating that the second condition of the user has a value that exceeds the second threshold;

assign, based on the identified first of the second biometric trait measurements, the first category identification value to the first spatial region corresponding to the spatial location value associated with the identified first of the second biometric trait measurements; and assign, based on the identified second of the second biometric trait measurements, the second category identification value to the second spatial region corresponding to the spatial location value associated with the identified second of the second biometric trait measurements.

8. The system of claim 1, further comprising:

a plurality of biometric devices and a plurality of biometric data collection devices, wherein each of the biometric devices and each of the biometric data collection devices is configured to provide to the spatial categorization system biometric trait measurements of a different user; and wherein the spatial categorization system is configured to assign, based on the biometric trait measurements received from the plurality of biometric data collection devices, a category identification value to each of a plurality of spatial regions in which the biometric devices are operated.

9. A method, comprising:

measuring, by a first biometric sensing device, a first biometric trait of a user at least 512 times per second; wherein the first biometric sensing device is an electroencephalography (EEG) device having an EEG sensor; and the first biometric trait is electrical activity in a brain of the user measured by the EEG sensor;

assigning a timestamp to each measurement of the first biometric trait;

transmitting, using a first wireless transceiver circuit, measurements of the first biometric trait to a biometric data collection device via a wireless personal area network;

measuring, by a second biometric sensing device, a second biometric trait of the user;

transmitting measurements of the second biometric trait to the biometric data collection device via the wireless personal area network;

receiving the first biometric trait in the biometric data collection device using a second wireless transceiver circuit;

determining, by a positioning system of the biometric data collection device, spatial location values defining a spatial location of the biometric data collection device;

assigning a timestamp to each spatial location value;

transmitting, by the biometric data collection device using a third wireless transceiver circuit, the measurements of the first biometric trait and the spatial location values to a spatial categorization system via a wide area network;

transmitting, by the biometric data collection device, the measurements of the second biometric trait to the spatial categorization system via the wide area network;

storing the measurements of the first biometric trait, the measurements of the second biometric trait, and the spatial location values in a database;

retrieving from the database a biometric dataset including at least 10 gigabytes of measurements of the first biometric trait and the measurements of the second biometric trait;

processing each of the measurements of the first biometric trait and the measurements of the second biometric trait of the biometric data set, the processing including:

identifying, by the spatial categorization system, each first of the measurements of the first biometric trait, wherein each first of the measurements of the first biometric trait indicates that a first condition of the user has a value that exceeds a first threshold;

identifying, by the spatial categorization system, each first of the measurements of the second biometric trait, wherein each first of the measurements of the second biometric trait indicates that the first condition of the user has a value that exceeds the first threshold; and assigning, by the spatial categorization system, based on the first of the measurements of the first biometric trait and the first measurement of the second biometric trait, a first category identification value to a first spatial region corresponding to a spatial location value associated by the time stamps with the first of the measurements of the first biometric trait;

identifying, by the spatial categorization system, each second of the measurements of the first biometric trait, wherein each second of the measurements of the first biometric trait indicates that a second condition of the user has a value that exceeds a second threshold; and assigning, by the spatial categorization system, based on the second of the measurements of the first biometric trait, a second category identification value to a second spatial region corresponding to the spatial location values associated by the time stamps with the second of the measurements of the first biometric trait; and generating a map of a geographic area including:
an indicator of the first category identification value in the first spatial region; and
an indicator of the second category identification value in the second spatial region.

10. The method of claim 9, wherein the biometric data collection device is a cellular handset, and the wide area network comprises a cellular data communication network.

11. The method of claim 9, further comprising:
identifying, by the spatial categorization system, a second of the measurements of the second biometric trait indicating that a second condition of the user has a value that exceeds a second threshold; and assigning, by the spatial categorization system, based on the second of the measurements of the second biometric trait, the second category identification value to the second spatial region corresponding to the spatial location values associated by the time stamps with the measurements of the second biometric trait.

12. The method of claim 9, wherein measuring the second biometric trait comprises acquiring heart rate signals from the user.

* * * * *